(12) United States Patent
Rudolph et al.

(10) Patent No.: US 8,653,484 B2
(45) Date of Patent: Feb. 18, 2014

(54) DETECTION OF EMISSION RADIATION OF UV LIGHT EMITTING DIODE BY STRUCTURALLY IDENTICAL UV LIGHT RECEIVING DIODE

(71) Applicant: Atlas Material Testing Technology GmbH, Linsengericht-Altenhasslau (DE)

(72) Inventors: Bernd Rudolph, Alzenau (DE); Peter March, Frankfurt am Main (DE)

(73) Assignee: Atlas Material Testing Technology GmbH, Linsengericht-Altenhasslau (DE)

( * ) Notice: Subject to any disclaimer, the term of this patent is extended or adjusted under 35 U.S.C. 154(b) by 0 days.

(21) Appl. No.: 13/934,899

(22) Filed: Jul. 3, 2013

(65) Prior Publication Data

US 2014/0008551 A1    Jan. 9, 2014

(30) Foreign Application Priority Data

Jul. 5, 2012   (EP) .................................... 12175185

(51) Int. Cl.
*A61N 5/00*    (2006.01)
*G21G 5/00*    (2006.01)

(52) U.S. Cl.
USPC ................... 250/492.1; 250/372; 250/504 R; 250/252.1; 250/395

(58) Field of Classification Search
USPC ............... 250/372, 504 R, 492.1, 252.1, 395
See application file for complete search history.

(56) References Cited

U.S. PATENT DOCUMENTS

| 5,126,826 | A  | * | 6/1992 | Kauchi et al. ................. 257/461 |
| 6,872,936 | B2 | * | 3/2005 | Rathod et al. ................... 850/63 |
| 2005/0087768 | A1 | * | 4/2005 | March et al. ................... 257/200 |
| 2006/0049360 | A1 |   | 3/2006 | Schoenlein et al. |
| 2010/0005911 | A1 | * | 1/2010 | Scott et al. ................... 73/865.6 |
| 2011/0079071 | A1 |   | 4/2011 | Schultz et al. |

FOREIGN PATENT DOCUMENTS

DE            103 50 020 B3    5/2005
DE       10 2004 037 603 B3   10/2005

OTHER PUBLICATIONS

European Search Report mailed Dec. 5, 2012 in corresponding European Application No. 12175185.3.

\* cited by examiner

*Primary Examiner* — Jack Berman
*Assistant Examiner* — Meenakshi Sahu

(57) ABSTRACT

A UV light emitting diode (UV-LED) is arranged in a weathering chamber and a UV light receiving diode, which is constructed on the same material basis as the UV LED, is arranged relative to the UV LED in such a way that a portion of the radiation emitted by the UV LED impinges on the UV light receiving diode during the operation of the device.

16 Claims, 3 Drawing Sheets

DETECTION OF EMISSION RADIATION OF UV LIGHT EMITTING DIODE BY STRUCTURALLY IDENTICAL UV LIGHT RECEIVING DIODE

CROSS REFERENCE TO RELATED APPLICATIONS

This application is based on and hereby claims priority to European Patent Application No. 12 175 185.3 filed on Jul. 5, 2012, the contents of which are hereby incorporated by reference.

BACKGROUND

The present invention relates to a device for artificially weathering or testing the lightfastness of samples, to a UV radiation device, and to a method for operating a device for artificially weathering or testing the lightfastness of samples.

In devices for artificial weathering, an assessment of the weather-governed aging behavior of a sample, in particular of a planar material sample, is carried out, wherein the sample is subjected to artificial weathering. Such devices usually comprise for this purpose a weathering chamber, in which mounting means for the mounting of samples to be weathered and a radiation source for applying radiation, in particular UV radiation, to the samples are arranged.

In such devices for artificially weathering or testing the lightfastness of material samples, the intention usually is to estimate the service life of materials which, in the application thereof, are constantly exposed to natural weather conditions and thus deteriorate under climatic influences such as sunlight, heat from the sun, moisture and the like. In order to obtain a good simulation of the natural weather circumstances, it is advantageous if the spectral energy distribution of the light generated in the device corresponds as much as possible to that of the natural solar radiation, for which reason xenon emitters have been used as radiation source hitherto in such devices. In addition, a time-lapse aging test of the materials is substantially obtained by the samples being irradiated in a manner greatly intensified relative to the natural conditions, whereby the aging of the samples is accelerated. Consequently, after a comparatively short time it is possible to make a statement about the long term aging behavior of a material sample.

The material samples examined in artificial weathering devices for the most part consist of polymeric materials. In the latter, the weather-governed deterioration is substantially brought about by the UV component of the solar radiation. The photochemical primary processes that take place here, that is to say the absorption of photons and the generation of excited states or free radicals, are temperature-independent. By contrast, the subsequent reaction steps with the polymers or additives can be temperature-dependent, with the result that the observed aging of the materials is likewise temperature-dependent.

In the weathering test devices known hitherto, a xenon lamp is usually used as radiation source. Although, as is known, the solar spectrum can be simulated very well with this lamp, the emitted radiation has a relatively high spectral component in the infrared spectral range, which has to be suppressed by filters in order to prevent the samples from being heated to an excessively great extent. Moreover, a commercially available xenon radiation source has only a service life of approximately 1500 hours.

Furthermore, a metal halide lamp can also be used as radiation source, but this lamp has the disadvantage that it cannot be regulated, or can be regulated only with great difficulty. The same also applies to fluorescent lamps, which have likewise already been used as radiation sources in weathering test devices and are disadvantageously associated with a relatively short service life.

Furthermore, all the radiation sources mentioned have the disadvantage that they are not spectrally variable.

A further disadvantage of the above-mentioned conventional radiation sources of weathering test devices is that the latter are relatively unwieldy in accordance with their construction and their driving and therefore cannot be adapted for example to changed conditions with regard to the sample surfaces of the material samples to be irradiated.

SUMMARY

Therefore, it is an object of the present invention to configure a device for artificial weathering or testing lightfastness such that the emission radiation of a UV light emitting diode contained in the device can be detected in a suitable manner.

This object is achieved by means of the features of the independent patent claims. Advantageous configurations and developments of the invention are specified in the dependent claims.

Accordingly, in accordance with a first aspect, the invention relates to a device for artificially weathering or testing the lightfastness of samples, said device comprising a weathering chamber, in which a UV light emitting diode (UV LED) and a UV light receiving diode are arranged. The UV light receiving diode is constructed on the same material basis as the UV LED and is arranged relative to the UV LED in such a way that a portion of the radiation emitted by the UV LED impinges on the UV light receiving diode during the operation of the device. In particular, it can be provided that the UV light receiving diode has the same internal construction, such as in particular the same semiconductor layer structure, as the UV LED.

In accordance with a second aspect, the invention relates to a UV radiation device which can be used in a device in accordance with the first aspect. All features and developments described in this application in relation to the device in accordance with the first aspect apply in the same way to the UV radiation device in accordance with the second aspect.

The present invention is thus based on a significant insight according to which a UV light receiving diode having the highest possible sensitivity can be provided by being embodied structurally identically to the UV light emitting diode whose emission radiation is intended to be detected by said UV light receiving diode. Such a UV light receiving diode can have a spectral absorption band which substantially corresponds to the spectral emission band of the UV light emitting diode. In particular, it can be provided that the maxima of the absorption band of the UV light receiving diode and the emission band of the UV light emitting diode are at one and the same wavelength or at least relatively close together.

A significant advantage over other arrangements is that a spectrally specific receiver is already present with the devices specified above. If a spectrally broadband UV receiver were used, then for the measurement of the output power of one of a plurality of different UV LEDs a filter transmissive to the wavelength of said UV LED would have to be arranged upstream of the UV receiver.

In accordance with one embodiment of the device, in this case it is possible to adopt a procedure such that two identical UV light emitting diodes or at least two UV light emitting diodes which are nominally identical or identical in accordance with manufacturer specifications are provided and one of them when incorporated into a sample chamber of a device for artificial weathering or testing lightfastness is used and correspondingly electrically interconnected as a UV light receiving diode. In this case, it may prove to be advantageous if two UV light emitting diodes from one and the same batch from a manufacturer are used in order to ensure that both UV light emitting diodes have undergone one and the same production process, in particular one and the same process sequence during the production of the semiconductor layer structure in a process chamber. This makes it possible to ensure that the two UV light emitting diodes have as exactly as possible the same semiconductor layer structure and the UV light receiving diode used by both UV light emitting diodes later during operation thus corresponds, with regard to its spectral absorption behavior, as exactly as possible to the spectral emission behavior of the UV light emitting diode to be measured. For this case, a maximum sensitivity of the UV light receiving diode during operation can then be expected.

In accordance with one embodiment of the device, a UV light receiving diode is arranged in such a way that radiation from a plurality of UV LEDs that is emitted during the operation of the device impinges on the UV receiving diode, wherein UV light emitting diodes having the same output wavelength are then preferably involved.

In accordance with one embodiment, the device comprises a plurality of classes of UV LEDs having different emission bands, and a corresponding plurality of UV light receiving diodes, wherein each of the UV light receiving diodes is produced on the same material basis as a UV LED of one class, in particular has an internal construction identical thereto or semiconductor layer structure identical thereto. Accordingly, it can be provided, for example, that a plurality or all of the UV LEDs of one class are assigned to a specific, structurally identical UV light receiving diode which is intended to detect the output radiation of said UV LEDs.

In accordance with one embodiment of the device, the one or the plurality of UV LEDs and the UV light receiving diode are arranged on a common carrier, in particular a circuit board.

In accordance with one embodiment of the device, the one or the plurality of UV LEDs are arranged on a common carrier and the UV light receiving diode is arranged on a different carrier. In particular, it can be provided that the samples to be examined are arranged in a sample plane, opposite the UV radiation device, on a carrier suitable therefor and the one or the plurality of UV light receiving diodes are likewise arranged on said carrier.

In accordance with one embodiment of the device, the one or the plurality of UV LEDs and the UV light receiving diode are oriented in the same way. The UV LED is oriented for example such that it emits the UV radiation with its principal ray axis at a right angle with respect to the plane of the circuit board, and the UV light receiving diode can then be mounted onto the circuit board in a manner spatially oriented in the same way, such that it is likewise sensitive only to UV radiation which impinges on the UV light receiving diode in a direction perpendicular to the circuit board. In this case, if appropriate, care should be taken to ensure that the radiation emitted by the UV LED is fed to the UV light receiving diode in a suitable manner. This can be done, for example, by a suitably shaped coupling medium consisting of a suitable material, as will be explained in even greater detail further below on the basis of an exemplary embodiment.

In accordance with one embodiment of the device, the UV LED and the UV light receiving diode are not oriented in the same way, wherein the UV light receiving diode can be arranged in a tilted manner, for example, wherein it is advantageously tilted in the direction of the UV LED. In this way, if appropriate without using an additional coupling medium it is possible to feed the emission radiation of the UV LED to the UV light receiving diode. Nevertheless, in this case, too, it can be provided that such a coupling medium is used.

In accordance with one embodiment of the device, a coupling medium is arranged in the beam path of that portion of the radiation emitted by the UV LED which impinges on the UV light receiving diode, said coupling medium directing said portion of radiation onto the UV light receiving diode. In accordance with one embodiment, the coupling medium can be a plate that is transmissive to UV radiation, such as a quartz plate. In accordance with one embodiment, the coupling medium can be an optical fiber that is transmissive to UV radiation. In accordance with one embodiment, a layer that is non-transmissive to UV radiation can be applied on the coupling medium and can prevent stray radiation from penetrating into the coupling medium and the stray radiation from impinging of the UV light receiving diode.

In accordance with one embodiment, the device comprises at least one further UV LED, wherein a portion of the radiation emitted by the further UV LED impinges on the UV light receiving diode during the operation of the device. In the case where a coupling medium is used, the further UV LED and the coupling medium can be arranged relative to one another in such a way that, during the operation of the device, a portion of the radiation emitted by the further UV LED is directed onto the UV light receiving diode by the coupling medium. It can be provided, for example, that the portion of radiation of the first UV LED is coupled into the coupling medium at a light entrance end of the coupling medium and the portion of radiation of the further LED is coupled into the coupling medium at an opposite light entrance end of the coupling medium and both portions of radiation are then directed within the coupling medium onto the UV light receiving diode. In this case, too, the coupling medium can be provided either by a plate, in particular flat plate, for example quartz plate, or else an optical fiber.

In accordance with one embodiment of the device, the UV light receiving diode can optionally be operated as a UV light receiving diode or as a UV LED. For this purpose, the external electrical interconnection can be embodied in such a way that, in a switching configuration for light emission, a voltage in the forward direction of the diode can be applied and a current can be injected into the diode and, in a switching configuration for light reception, a different voltage, if appropriate a voltage in the reverse direction of the diode, can be applied to the diode and an electrical current generated by the diode on account of light incidence can be detected.

The present invention likewise relates to a method for operating a device for artificially weathering or testing the lightfastness of samples in accordance with a third aspect, wherein the method comprises the following steps:
a. providing a weathering chamber;
b. providing at least two UV semiconductor diodes on the same material basis, in particular having an identical internal construction or identical semiconductor layer structure;
c. arranging a first of the two UV semiconductor diodes in the weathering chamber and operating the first UV semiconductor diode as a UV light emitting diode; and
d. arranging a second of the two UV semiconductor diodes in the weathering chamber; and
e. operating the second semiconductor diode as a UV light receiving diode, wherein the second UV semiconductor diode is arranged relative to the first UV semiconductor diode in such a way that a portion of the radiation emitted by the first UV semiconductor diode impinges on the second UV semiconductor diode during the operation of the device.

In accordance with one embodiment of the method, in step b. a plurality of classes of UV LEDs having different emission bands and a plurality of UV light receiving diodes are provided, each of the UV light receiving diodes is constructed on the same material basis as a UV LED of one class, in particular has an internal construction identical thereto or semiconductor layer structure identical thereto. In this case, it can be provided, in particular, that the plurality of classes of UV LEDs having different emission bands are chosen in such a way that a spectral distribution with which a specific spectral UV characteristic is approximated can be obtained. In particular, the rising edge of the UV component of natural solar radiation at the short-wave end can be approximated with the UV LEDs. However, it is also possible to approximate a UV emission band of a known UV light source or some other arbitrarily defined UV characteristic.

In accordance with one embodiment of the method, during operation the one or the plurality of UV LEDs can be regulated on the basis of output signals of the one or the plurality of UV light receiving diodes. A simple type of regulation can consist, for example, in evaluating a decrease in the radiation intensity that is detected by the UV light receiving diode. However, more complicated types of regulations are also conceivable in which, for example, the radiation power of each of the UV LEDs having different emission bands is regulated in such a way that the spectral distribution in the plane of the samples to be examined is as spatially homogeneous as possible or, to put it another way, that a spatial inhomogeneity of said spectral distribution is limited to predefined deviations. The desired spectral distribution can in turn at the sample plane be such that the UV component of natural solar radiation, in particular the rising edge lying in the UV range, or some other desired UV characteristic is approximated as well as possible.

BRIEF DESCRIPTION OF THE DRAWINGS

The invention is explained in even greater detail below on the basis of exemplary embodiments in conjunction with the figures of the drawing, in which.

DETAILED DESCRIPTION OF THE PREFERRED EMBODIMENT

Figure 1:
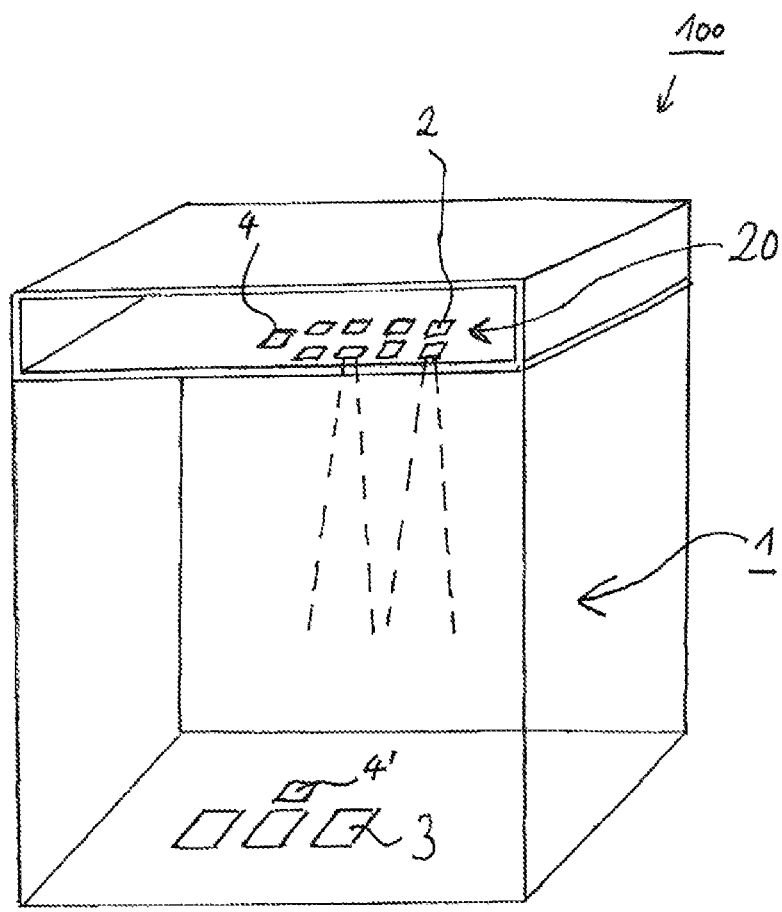
FIG. 1 shows an exemplary embodiment of a device according to the invention for artificially weathering or testing the lightfastness of samples in a perspective view.

FIG. 1 illustrates schematically in perspective view an embodiment for a device for artificial weathering or testing lightfastness. The device comprises a weathering chamber 1, in which a UV radiation device 20 is arranged. In the lower region of the sample chamber 1, suitable mounting means can be present on a baseplate, a number of samples 3 being able to be mounted by means of said mounting means. The device is therefore designed as a weathering device with stationary sample mounting. However, the invention can likewise be applied to weathering devices comprising movable sample mounts.

The UV radiation device 20 can comprise a plurality of UV LEDs 2, which can for example be mounted along the rows and columns of a matrix on a planar area, such as a circuit board, for example, and can be aligned with regard to their emission characteristic in such a way that the emission radiation is directed perpendicularly downward onto the samples 3 to be examined. In one practicable embodiment, the circuit board with the UV LEDs fixed on the lower surface thereof can be provided as part of an insert cassette that can be inserted into a slot provided therefor on the top side of the device 100. In this case, the circuit board forms a lower base area of the insert cassette, while a cooling medium can flow through the spatial region located thereabove, in order to efficiently dissipate the heat generated by the UV LEDs.

It goes without saying that the device 100 can contain further elements which serve for weathering the samples 3 and are not shown here merely for reasons of simplifying the illustration.

The UV LEDs 2 can be mounted on a common circuit board. One or a plurality of UV light receiving diodes 4 can likewise be mounted on said circuit board, and can detect in each case part of the radiation emitted by the UV LEDs 2. One exemplary embodiment further below describes how the radiation can be fed to the UV light receiving diode 4. As an alternative or in addition to the UV light receiving diode 4 arranged in the plane of the UV LEDs 2, a UV light receiving diode 4' can be arranged in the same plane of the samples 3. The UV light receiving diodes 4 and/or 4' are constructed on the same material basis as the UV LEDs 2 or a specific class of UV LEDs 2 having a specific UV emission band. Within the UV LEDs 2 a specific number of different classes corresponding to different UV emission bands can be present and a corresponding number of different UV light receiving diodes 4 and/or 4' can be present in order to detect the emitted radiation of the different UV LEDs 2 of the different classes.

Figure 2:
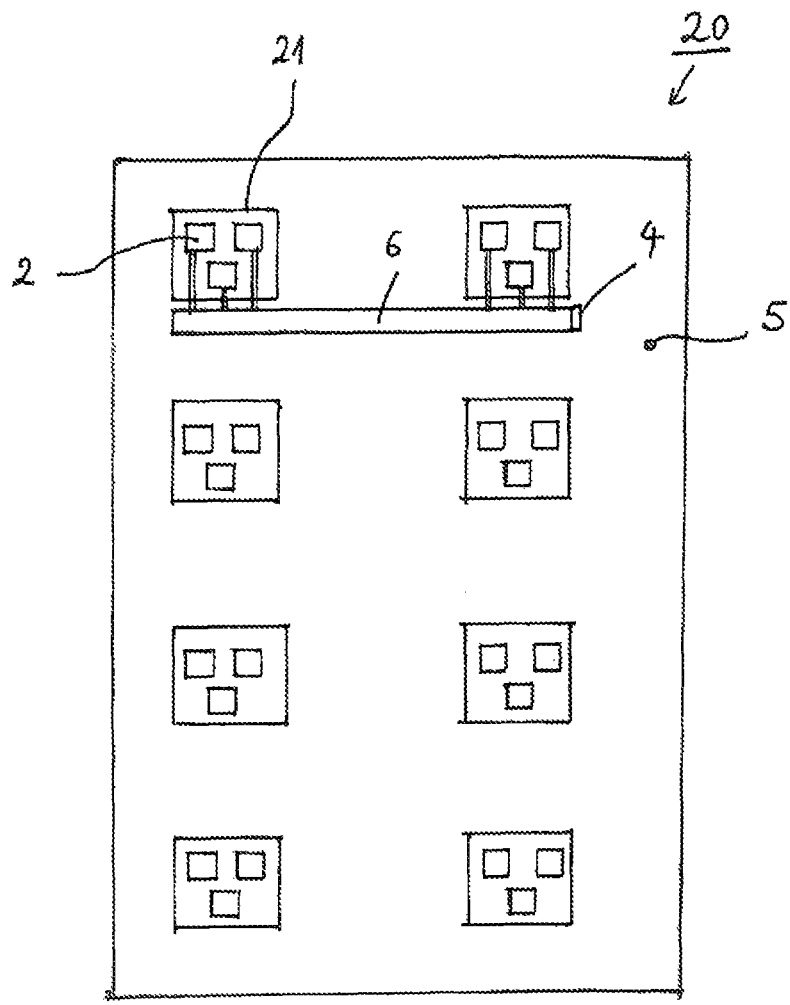
FIG. 2 shows a plan view of a UV radiation module comprising a UV LED and a UV light receiving diode.

FIG. 2 shows a plan view of a UV radiation module or a UV radiation device in accordance with one embodiment. The UV radiation module 20 generally comprises—as already shown in FIG. 1—a plurality of UV LEDs 2. The UV LEDs 2 can be mounted on a flat, rectangular carrier 5, which can be provided by a circuit board. The UV radiation module 20 can—in FIG. 1—be fixed in a device 100 for artificially weathering or testing the lightfastness of samples. In contrast to the arrangement in FIG. 1, the UV LEDs 2 are not distributed spatially identically, but rather are combined in groups 21, wherein the groups 21 can be formed identically. In the exemplary embodiment illustrated, the groups each contain three UV LEDs 2 having different UV emission bands, in order to approximate therewith, for example, a specific desired spectral UV characteristic such as, for instance, the UV rising edge of the solar radiation. However, the groups 21 can also contain for example in each case only two UV LEDs having different emission bands. However, each of the groups can also contain more than three UV LEDs having different UV emission bands. If appropriate, UV LEDs of specific classes, that is to say having specific UV emission bands, can also be represented multiply in the groups.

A coupling medium such a quartz glass block 6 can be mounted on the circuit board 5 below the upper row of groups 21, into which block part of the radiation emitted by the UV LEDs 2 can be coupled. One or a plurality of UV light receiving diodes 4 on which the radiation impinges can be mounted onto the quartz glass block 6 at the outer right end thereof. By way of example, three different UV light receiving diodes 4 can be present, each of which is constructed on the same material basis as a specific UV LED 2 of the two groups 21. The partial radiation beams of the individual UV LEDs 21 can be coupled into the quartz glass block 6 from the UV LEDs 21 by optical fiber segments. During the operation of the device 20, a portion of the radiation emitted by a UV LED 2 impinges on a specific UV receiving diode 4. The UV receiving diode 4 can be identical to the UV LED 2 in terms of its internal layer construction, such that its spectral absorption characteristic substantially corresponds to the spectral emission characteristic of the UV LED 2 and it thus has an optimum sensitivity for the radiation emitted by the UV LED 2. In particular, the UV light receiving diode 4 can originally likewise be a UV LED which is now used as a UV light receiving diode merely with regard to its external electrical interconnection. Advantageously, therefore, the UV LED 2 and the UV light receiving diode 4 have originally been produced by the manufacturer as UV LEDs together during one and the same production process, in particular the layers of the semiconductor layer structure of both diodes have been grown with within one and the same process chamber.

It can furthermore be provided that the UV LEDs 2 within a group are spaced apart from one another in such a way that the distances are negligible relative to the distance between the UV radiation device 20 and the sample plane. This has the consequence that each group 21 taken by itself generates on the sample plane a spectrum which is mixed ("finished") in the desired manner. The distance between the UV LEDs 2 can be determined as, for example, an average value of the distances between the mid points of in each case directly adjacent UV LEDs and this distance can be less than 10 times, 50 times or 100 times the distance between the UV radiation device 20 and the sample plane.

It is also conceivable for the external electrical interconnection of the UV light receiving diode 4 to be embodied in such a way that the latter can optionally be used as a UV LED or UV light receiving diode.

Figure 3:
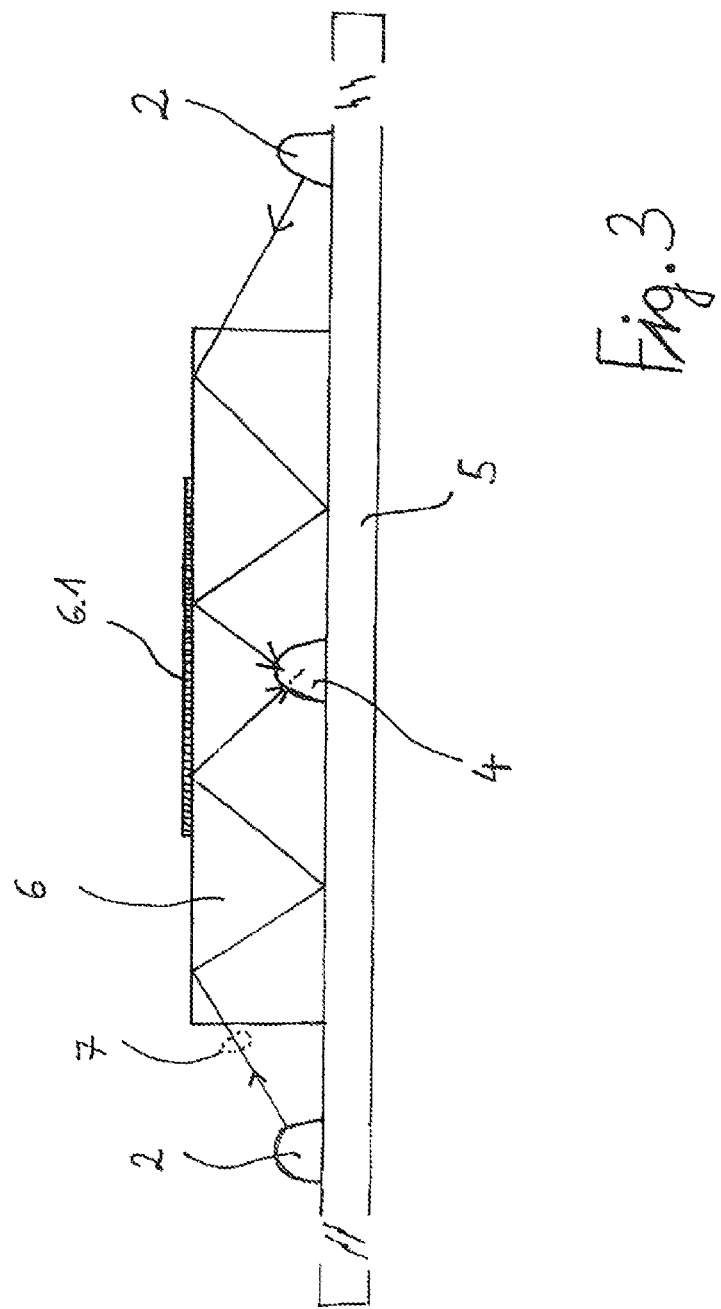
FIG. 3 shows a lateral cross-sectional view of an arrangement comprising a UV LED, a UV light receiving diode and a coupling medium arranged between both.

FIG. 3 illustrates a lateral cross-sectional view of an arrangement comprising two UV LEDs 2, a UV light receiving diode 4 and a coupling medium 6 arranged between both. The components mentioned can be mounted on a carrier 5 such as a circuit board. The left-hand one of the two UV LEDs 2 is oriented such that its principal emission direction is directed upward perpendicular to the plane of the carrier 5 and, assuming a Lambertian emitter in accordance with a cosine function, the radiation power decreases as the angle with respect to the emission direction increases. The radiation emitted at a small angle with respect to the plane of the carrier 5 can be taken up by a suitable, UV-transmissive coupling medium 5 and forwarded in the direction toward the UV receiving diode 4. In the exemplary embodiment shown, the coupling medium 6 can in turn be formed by a quartz plate, which can be fixed by its lower surface on the carrier 5 directly above the UV light receiving diode 4. The quartz plate 6 can be embodied such that at its lower surface it has an indentation that can accommodate the UV light receiving diode 4. At its light entrance end the quartz plate 6 captures part of the radiation emitted by the UV LED 2 in the form of a radiation beam 7. Part of this radiation beam can in turn pass into the UV light receiving diode 4 by way of total internal reflection at the upper and lower surfaces of the quartz plate 6. A layer 6.1 that is non-transmissive to UV radiation can be applied on the upper surface of the quartz plate 6 and prevents UV stray radiation in the sample chamber from impinging on the UV light receiving diode 4.

It can furthermore be provided that at a further light entrance end of the quartz plate 6, a portion of radiation of a further, right-hand UV LED 2 is coupled in and fed to the UV light receiving diode 4. The quartz plate 6 can also be embodied such that at further light entrance ends, portions of radiation from further UV LEDs 2 are coupled in and fed to the UV light receiving diode 4.

Instead of a quartz plate as coupling medium 6 it is also possible to use a UV-transmissive optical fiber. The light entrance end of the optical fiber could be brought practically as close as desired to the UV LED 2. The optical fiber can be provided with a UV-non-transmissive coating for example on part of its circumference, in order to prevent UV stray radiation from being coupled in.

Although specific embodiments have been illustrated and described in this description, it is evident to the person skilled in the art that the specific embodiments shown and described can be exchanged for a variety of alternative and/or equivalent implementations, without departing from the scope of protection of the present invention. This application is intended to cover any adaptations or variations of the specific embodiments discussed herein. It is therefore envisaged that this invention is limited only by the claims and the equivalents thereof.

What is claimed is:

1. A device for artificially weathering or testing the lightfastness of samples comprising:
   a weathering chamber;
   an ultraviolet radiation device arranged in the weathering chamber and having at least one ultraviolet light emitting diode; and
   an ultraviolet light receiving diode, which is constructed on the same material basis as the ultraviolet light emitting diode and is arranged relative to the ultraviolet light emitting diode in such a way that a portion of the radiation emitted by the ultraviolet light emitting diode impinges on the ultraviolet receiving diode during the operation of the device.

2. The device as claimed in claim 1, further comprising:
   a plurality of classes of ultraviolet light emitting diodes having different emission bands; and
   a corresponding plurality of ultraviolet light receiving diodes, wherein each of the ultraviolet light receiving diodes is constructed on a same material basis as any ultraviolet light emitting diode in one class.

3. The device as claimed in claim 1, wherein the ultraviolet light emitting diode and the ultraviolet light receiving diode are arranged on a common carrier, in particular a circuit board.

4. The device as claimed in claim 1, wherein the ultraviolet light emitting diode and the ultraviolet receiving diode are oriented in the same way.

5. The device as claimed in claim 1, wherein the ultraviolet light emitting diode and the ultraviolet receiving diode are not oriented in the same way, in particular are tilted relative to one another.

6. The device as claimed in claim 1, wherein a coupling medium is arranged in the beam path of the portion impinging on the ultraviolet light receiving diode, said coupling medium directing the portion onto the ultraviolet light receiving diode.

7. The device as claimed in claim 6, wherein the coupling medium is a plate that is transmissive to ultraviolet radiation.

8. The device as claimed in claim 1, comprising at least one further ultraviolet light emitting diode, wherein a portion of the radiation emitted by the further ultraviolet light emitting diode impinges on the ultraviolet light receiving diode during the operation of the device.

9. The device as claimed in claim 8, wherein the further ultraviolet light emitting diode and the coupling medium are arranged relative to one another in such a way that, during the operation of the device, a portion of the radiation emitted by the further ultraviolet light emitting diode is directed onto the ultraviolet light receiving diode by the coupling medium.

10. The device as claimed in claim 6, wherein the further ultraviolet light emitting diode and the coupling medium are arranged relative to one another in such a way that, during the operation of the device, a portion of the radiation emitted by the further ultraviolet light emitting diode is directed onto the ultraviolet light receiving diode by the coupling medium.

11. An ultraviolet radiation device, comprising
a plurality of ultraviolet light emitting diodes, and an ultraviolet light receiving diode, which is constructed on the same material basis as the ultraviolet light emitting diodes and is arranged relative to the ultraviolet light emitting diodes in such a way that a portion of the radiation emitted by the ultraviolet light emitting diodes impinges on the ultraviolet receiving diode during the operation of the device.

12. A method for operating a device for artificially weathering or testing the lightfastness of samples, comprising:
   a. providing a weathering chamber;
   b. providing at least two ultraviolet semiconductor diodes on the same material basis;
   c. arranging a first of the two ultraviolet semiconductor diodes in the weathering chamber and operating the first ultraviolet semiconductor diode as a ultraviolet light emitting diode; and
   d. arranging a second of the two ultraviolet semiconductor diodes in the weathering chamber; and
   e. operating the second semiconductor diode as an ultraviolet light receiving diode, wherein the second ultraviolet semiconductor diode is arranged relative to the first ultraviolet semiconductor diode in such a way that a portion of the radiation emitted by the first ultraviolet semiconductor diode impinges on the second ultraviolet semiconductor diode during the operation of the device.

13. The method as claimed in claim 12, wherein
in step b. a plurality of classes of ultraviolet light emitting diodes having different emission bands and a plurality of ultraviolet light receiving diodes are provided, wherein
each of the ultraviolet light receiving diodes is constructed on the same material basis as an ultraviolet light emitting diode in one class.

14. The method as claimed in claim 13, wherein in step b. the plurality of classes of ultraviolet light emitting diodes having different emission bands are chosen in such a way that a specific spectral ultraviolet characteristic is approximated.

15. The method as claimed in claim 12, further comprising regulating the operation of the ultraviolet light emitting diode on the basis of an output signal of the ultraviolet light receiving diode.

16. The method as claimed in claim 12, further comprising regulating the operation of the ultraviolet light emitting diodes on the basis of output signals of the ultraviolet light receiving diodes.

* * * * *